United States Patent
Fellenz et al.

(10) Patent No.: US 12,329,685 B2
(45) Date of Patent: Jun. 17, 2025

(54) COUNTERBALANCE MECHANISM IN OPHTHALMIC LASER SYSTEM EMPLOYING A VARIABLE BEAM BALANCE TO PROVIDE A VARIABLE NET LOAD

(71) Applicant: AMO Development, LLC, Irvine, CA (US)

(72) Inventors: Frank D. Fellenz, San Jose, CA (US); Roger Accurso, Corning, CA (US); Jorge Haro, Santa Clara, CA (US)

(73) Assignee: AMO Development, LLC, Irvine, CA (US)

( * ) Notice: Subject to any disclaimer, the term of this patent is extended or adjusted under 35 U.S.C. 154(b) by 306 days.

(21) Appl. No.: 17/808,086

(22) Filed: Jun. 21, 2022

(65) Prior Publication Data

US 2023/0000674 A1 Jan. 5, 2023

Related U.S. Application Data

(60) Provisional application No. 63/202,946, filed on Jun. 30, 2021.

(51) Int. Cl.
*A61F 9/009* (2006.01)
*A61F 9/008* (2006.01)

(52) U.S. Cl.
CPC .... *A61F 9/009* (2013.01); *A61F 2009/00844* (2013.01)

(58) Field of Classification Search
CPC ............................................ A61F 2009/00844
See application file for complete search history.

(56) References Cited

U.S. PATENT DOCUMENTS

| | | | |
|---|---|---|---|
| 6,129,319 A | * | 10/2000 | Metelski ................ G02B 7/001 359/384 |
| 6,386,322 B1 | | 5/2002 | McCormick |
| 8,337,490 B2 | | 12/2012 | Robl |

(Continued)

FOREIGN PATENT DOCUMENTS

| | | |
|---|---|---|
| CN | 102834755 B | 9/2015 |
| CN | 105250071 B | 9/2018 |

(Continued)

*Primary Examiner* — Rex R Holmes
*Assistant Examiner* — Jennifer L Ghand

(57) ABSTRACT

A counterbalance mechanism in an ophthalmic laser system balances the weight of the laser beam delivery head and provides small, precise and repeatable variations in the net load exerted by the laser head on the patient's eye over a defined distance of travel. The counterbalance mechanism includes a balance beam pivotably mounted on a support block, with the laser head and a counterweight mounted on its two ends. The counterweight is movable along the balance beam via a linear motion bearing. A mechanical link links the counterweight to the support block; the link has a predefined length and is pivotable around its respective connection points on the support block and the counterweight. When the balance beam pivots, the link causes the counterweight to move along the balance beam, thereby changing the mechanical advantage of the counterweight and varies the counterbalancing force to provide variations in the net load.

6 Claims, 6 Drawing Sheets

(56) References Cited

U.S. PATENT DOCUMENTS

| | | | |
|---|---|---|---|
| 8,858,539 | B2 | 10/2014 | Rathjen |
| 9,351,878 | B2 | 5/2016 | Muehlhoff et al. |
| 10,105,260 | B2 | 10/2018 | Raksi |
| 2016/0310317 | A1 | 10/2016 | Gooding et al. |
| 2017/0296384 | A1* | 10/2017 | Fleischmann .......... A61B 90/50 |
| 2017/0340483 | A1* | 11/2017 | Rill .................... A61F 9/00825 |
| 2019/0060121 | A1 | 2/2019 | Festag |

FOREIGN PATENT DOCUMENTS

| | | | |
|---|---|---|---|
| EP | 1731120 | B1 | 5/2008 |
| EP | 2119411 | A1 | 11/2009 |
| WO | 2011107113 | A1 | 9/2011 |
| WO | 2017182342 | A1 | 10/2017 |

\* cited by examiner

COUNTERBALANCE MECHANISM IN OPHTHALMIC LASER SYSTEM EMPLOYING A VARIABLE BEAM BALANCE TO PROVIDE A VARIABLE NET LOAD

CROSS-REFERENCE TO RELATED APPLICATIONS

This application claims the benefit under 35 U.S.C. § 119(e) of U.S. Provisional Patent Application No. 63/202,946, filed Jun. 30, 2021, which is incorporated herein by reference in its entirety.

BACKGROUND OF THE INVENTION

Field of the Invention

This invention relates to mechanical systems for counterbalancing a weight, and in particular, it relates to a counterbalance mechanism for a laser beam delivery head in an ophthalmic laser system.

Description of Related Art

Many mechanical systems require counterbalancing an object's weight to allow the object to be kept stationary or moved vertically by a relatively small force compared to the weight of the object. In one exemplary application, a laser beam delivery head of an ophthalmic laser system is typically heavy and needs to be counterbalanced so as to inhibit gravity-induced movement and to inhibit transfer of gravity-induced forces to the patient's eye coupled to the laser head.

More specifically, in an ophthalmic laser system, a laser beam delivery head contains various optical elements to deliver a laser beam to the patient's eye. A patient interface device of the laser head is mechanically coupled to the eye, with the patient in a supine position. The patient interface device typically includes a flexible suction ring to securely attach the patient interface device to the surface of the eye. Some patient interface devices also include a contact lens (also referred to as an applanation lens) that contacts the cornea surface of the eye, where a downward applanation force is applied by the applanation lens to applanate the cornea during the surgery.

The laser head in such ophthalmic laser systems are moveable in at least the vertical direction. Various types of mechanisms for counterbalancing the weight of the laser head have been described. Some such systems employ a spring mechanism for counterbalance. For example, U.S. Pat. Appl. Pub. No. 2016/0310317, entitled "Free Floating Patient Interface for Laser Surgery System," describes z axis springs implemented by metal tapes wound around spring loaded bearing spools as the counterbalance mechanism. Some other systems use a counterweight. For example, U.S. Pat. No. 8,337,490, entitled "Apparatus for Movable and Weight-Compensating Suspension of a Focusing Objective of a Laser System," describes a counterweight on a lever arm of a rocker, where a counterweight can be shifted manually along the lever arm so as to change the effective force application point of the counterweight and thus the effective counterforce moment.

SUMMARY

The present invention is directed to a counterbalance mechanism, in particular, a counterbalance mechanism in an ophthalmic laser system for counterbalancing the laser beam delivery head.

An object of the present invention is to provide a counterbalance mechanism that allow the large weight of the laser head to be counterbalanced while providing small, precise and repeatable variations in net load (force) exerted by the laser head on the patient's eye over a defined distance of travel of the laser head.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a counterbalance mechanism which includes: a support block; a balance beam pivotably mounted on the support block by a fulcrum, the balance beam having a first end and a second end located on opposite sides of the fulcrum; a load attached to the balance beam near the first end; a counterweight; a bearing configured to mount the counterweight to the balance beam near the second end, wherein the counterweight is movable along the balance beam via the bearing; and a mechanical link having first and second connection points and a predetermined length between the first and second connection points, pivotably connected at the first connection point to the support block at a location above the fulcrum, and pivotably connected at the second connection point to the counterweight, wherein the mechanical link is configured to move the counterweight along the balance beam when the balance beam pivots around the fulcrum. The load may be an laser beam delivery head of an ophthalmic laser system.

In another aspect, the present invention provides an ophthalmic laser system employing a counterbalance mechanism, which includes: a laser system frame; a gantry supported by the laser system frame; and a counterbalance system disposed within the gantry, including: a support block fixedly attached to the gantry; a balance beam pivotably mounted on the support block by a fulcrum, the balance beam having a first end and a second end located on opposite sides of the fulcrum; a laser beam delivery head attached to the balance beam near the first end; a counterweight; a bearing configured to mount the counterweight to the balance beam near the second end, wherein the counterweight is movable along the balance beam via the bearing; and a mechanical link having two connection points and a predetermined length between the two connection points, pivotably connected at one of the connection points to the support block at a location above the fulcrum, and pivotably connected at the other connection point to the counterweight, wherein the mechanical link is configured to move the counterweight along the balance beam when the balance beam pivots around the fulcrum.

In preferred embodiments, the mechanical link is configured to move the counterweight along the balance beam away from the fulcrum when the balance beam pivots in a direction that lifts the counterweight, and to move the counterweight along the balance beam toward the fulcrum when the balance beam pivots in a direction that lowers the counterweight.

In preferred embodiments, the weight of the laser beam delivery head and the weight of the counterweight are balanced when the balance beam is at a predefined pivot angle.

In another aspect, the present invention provides an ophthalmic laser system employing a counterbalance mechanism, which includes: a laser system frame; a gantry supported by the laser system frame; and a counterbalance system disposed within the gantry, including: a support block fixedly attached to the gantry; a balance beam pivotably mounted on the support block by a fulcrum, the balance beam having a first end and a second end located on opposite sides of the fulcrum; a laser beam delivery head attached to the balance beam near the first end; a counterweight; a bearing configured to mount the counterweight to the balance beam near the second end, wherein the counterweight is movable along the balance beam via the bearing; and an inclined slot disposed adjacent to the second end of the balance beam, the inclined slot extending outwardly as it extends upwardly, wherein a part of the counterweight is disposed in the inclined slot and slidable along the inclined slot, wherein the inclined slot is configured to move the counterweight along the balance beam when the balance beam pivots around the fulcrum.

In preferred embodiments, the inclined slot is configured to move the counterweight along the balance beam away from the fulcrum when the balance beam pivots in a direction that lifts the counterweight, and to move the counterweight along the balance beam toward the fulcrum when the balance beam pivots in a direction that lowers the counterweight. The inclined slot may be straight or curved.

In another aspect, the present invention provides an ophthalmic laser system employing a counterbalance mechanism, which includes: a laser system frame; a gantry supported by the laser system frame; and a counterbalance system disposed within the gantry, including: a support block fixedly attached to the gantry; an eccentric pulley mounted on support block; a circular pulley mounted on support block; a wire extending over the eccentric pulley and the circular pulley; a laser head is attached to one end of the wire closer to the circular pulley; and a counterweight attached to another end of the wire closer to the eccentric pulley.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the present invention provide a counterbalance mechanism for the laser head of an ophthalmic laser system. The counterbalance mechanism allows the large load of the laser head to be counterbalanced, while providing a small, precise and repeatable variation in net load (force) over a defined distance of travel of the laser head in the vertical direction. As described in detail with reference to FIG. 1, the counterbalance mechanism employs a balance beam that supports a counterbalance weight on a linear motion bearing. A geometric linkage varies the mechanical advantage of the weight and precisely varies the counterbalancing force to provide the variation in the net load.

Figure 1:
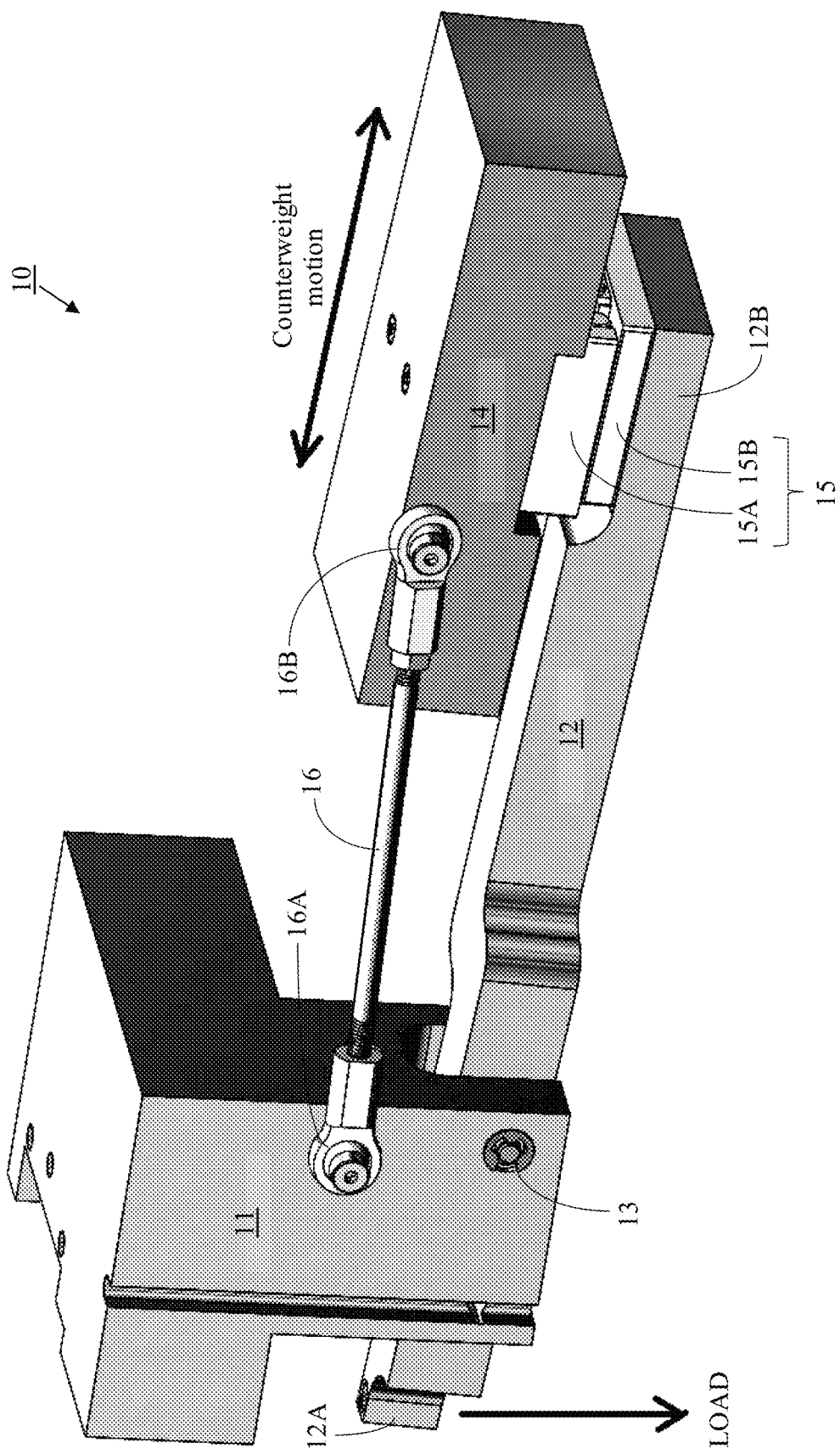
FIG. 1 illustrates a counterbalance mechanism in an ophthalmic laser system according to an embodiment of the present invention.

Referring to FIG. 1, the counterbalance mechanism 10 includes a support block 11 and a balance beam 12 pivotably supported by the support block 11 via a fulcrum (pivot) 13. The laser head, i.e., the object being counterbalanced, is mounted at a first end 12A of the balance beam 12, preferably by a vertical linear bearing to allow the laser head to maintain a vertical orientation when the balance beam 12 pivots. The laser head, which contains various optical elements, is not shown in FIG. 1 to avoid obscuring parts of the counterbalance mechanism, but the force it exerts on the balance beam 12 is indicated as the "LOAD" by the downward arrow.

A counterweight 14 is mounted on the balance beam 12 near the second end 12B via a linear motion bearing 15, so that the counterweight is able to move along the balance beam with negligible friction, as indicated by the double headed arrow. The linear motion bearing 15 may be implemented by any suitable mechanical components, such as rollers, slides, etc. The linear motion bearing 15 may include a first block 15A affixed to the counterweight 14 and a second block 15B affixed to the balance beam 12 near the second end 12B, the two blocks being moveable relative to each other along the direction of the balance beam.

The counterweight 14 is further linked to the support block 11 by a mechanical link 16, which may be implemented by a rigid member of any suitable shape, for example, a rod. One end of the link 16 is pivotably connected to the support block 11 by a first connection assembly 16A, at a location above the fulcrum 13, and the other end of the link is pivotably connected to the counterweight 14 by a second connection assembly 16B. It should be noted that the two connection points of the link 16 that are respectively connected to the support block 11 and counterweight 14 are not required to be at the two ends of the link 16, and the link is not required to have a straight shape; the operative geometric property of the link 16 is the length of the link, i.e., the linear distance between the two connection points. The connection assemblies 16A and 16B allow the link 16 to pivot around the respective axes of the connection assemblies. As will be described in detail later, the locations of the rotation axes of the two connection assemblies and the length of the link 16 partially determine the counterbalancing properties of the counterbalance mechanism. The length of the link 16 is fixed during an ophthalmic surgery, but may be adjustable for the purpose of system adjustment, e.g., to adjust the zero point of the balance beam 12, as will be described in more detail later. The adjustable length of the link 16 may be implemented, for example, by using a threaded rod with nuts at either or both ends.

In the particular embodiment of FIG. 1, the location of the connection assembly 16A on the support block 11 is directly above the pivot 13 in the vertical direction; the location of the connection assembly 16B on the counterweight 14 is above the balance beam and is offset from the center of gravity of the counterweight in the direction parallel to the balance beam. The connection locations of the link 16 is not limited to the example shown in FIG. 1.

Figure 2:
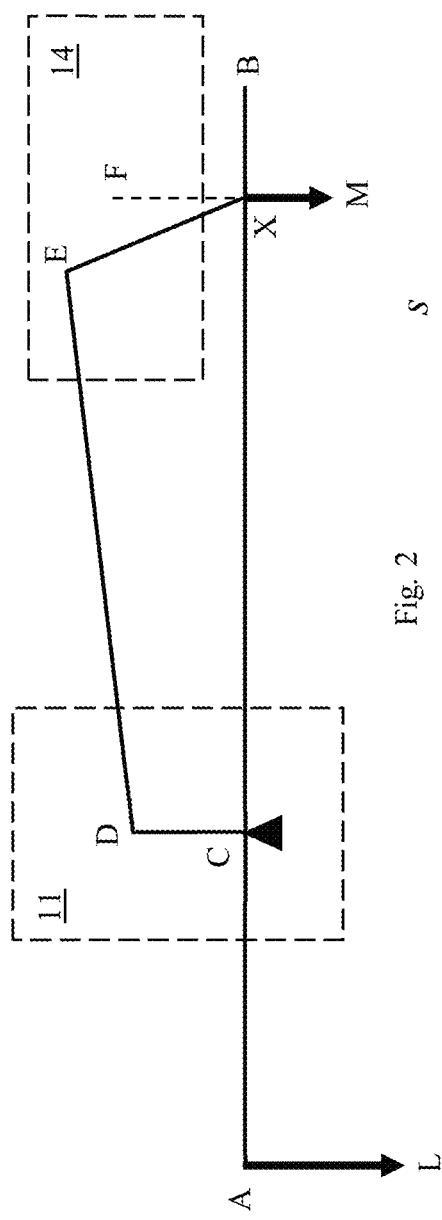
FIG. 2 schematically illustrates the geometric configuration of the various components of the counterbalance mechanism of FIG. 1.

The operating principle of the counterbalance mechanism is described with reference to FIGS. 2 and 3A-3C. The diagram in FIG. 2 schematically represents the geometric configuration of various components of the counterbalance mechanism of FIG. 1 in a side view. Line AB in FIG. 2 represents the balance beam 12, where point A represents the point where the load L acts on the balance beam. Point C represents the fulcrum 13 where the balance beam 12 is pivotably attached to the support block 11. Line DE represents the link 16, where point D represents the rotation axis of the connection assembly 16A on the support block 11, and point E represents the rotation axis of the connection assembly 16B on the counterweight 14.

The position of the counterweight 14 relative to the balance beam 12 may be defined as the perpendicular projection of a defined point on the counterweight onto the balance beam. In this example, it is defined as the perpendicular projection of the center of gravity of the counterweight (point F) onto the balance beam, as indicated by point X. Point X is a fixed point with respect to the counterweight 14 but is variable along the balance beam 12 (line AB), as the counterweight 14 is moveable along the balance beam via the linear motion bearing 15. Note here that when the balance beam 12 is horizontal, as is in the example of FIG. 2, point X is also the point where the weight M of the counterweight acts on the balance beam.

During operation, the weight M of the counterweight 14 is fixed; the orientation and length of line CD are fixed (it need not be vertical); and the lengths of line AC, line DE, and line EX are fixed. The angle CDE and angle DEX are variable (as the link 16 is pivotable around the connection assemblies 16A and 16B); the angle DCX is variable (as the balance beam 12 is pivotable around the fulcrum 13); and the angle EXC is fixed. The length of line CX is variable.

Given the above geometric constraints, the position of point X varies as a function of the angle DCB, i.e. the pivot angle of the balance beam 12. For example, from the position illustrated in FIG. 2 (where line AB is horizontal and point D is located above point C), if line AB rotates in the counter-clockwise direction around the pivot point C, point X will move away from the pivot C. Conversely, if line AB rotates in the clockwise direction, point X will move toward the pivot C. In other words, when the balance beam 12 pivots around the fulcrum 13, the counterweight 14 will slide along the balance beam via the bearing 15 due to the geometric constraint imposed by the link 16. In the meantime, when the balance beam 12 pivots, the point at which the weight M of the counterweight acts on the balance beam also shifts away from point X. The combined result of these movements and shifts is that the lever arm length for the counterweight M changes. This means, in turn, that the amount of load L required to balance the counterweight M changes. As will be described in more detail later, this results in a change of the applanation force exerted on the patient's eye.

Figure 3A:
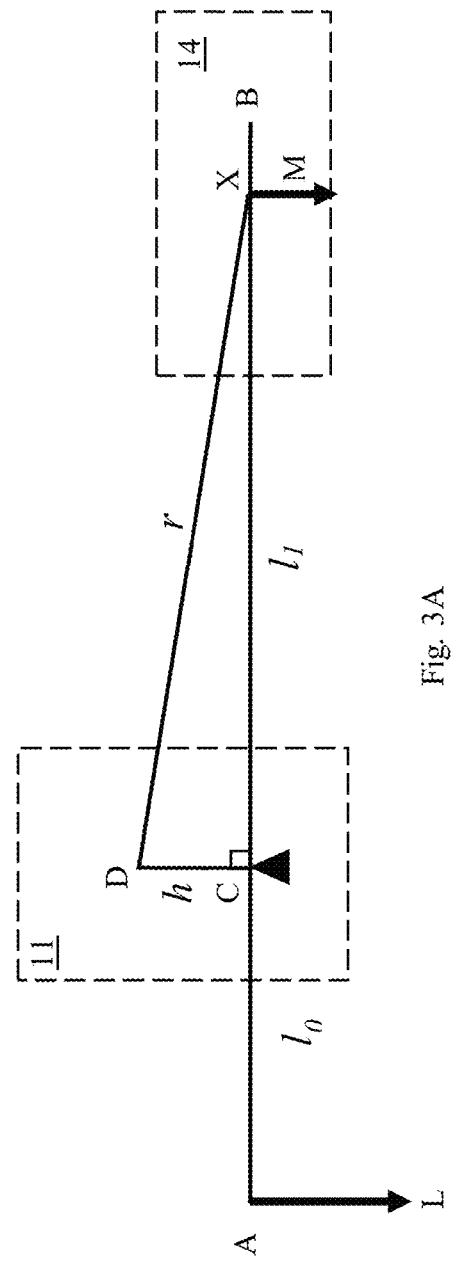
FIGS. 3A-3C schematically illustrates the geometric configuration and working principle of another counterbalance mechanism according to an embodiment of the present invention.
Figure 3B:
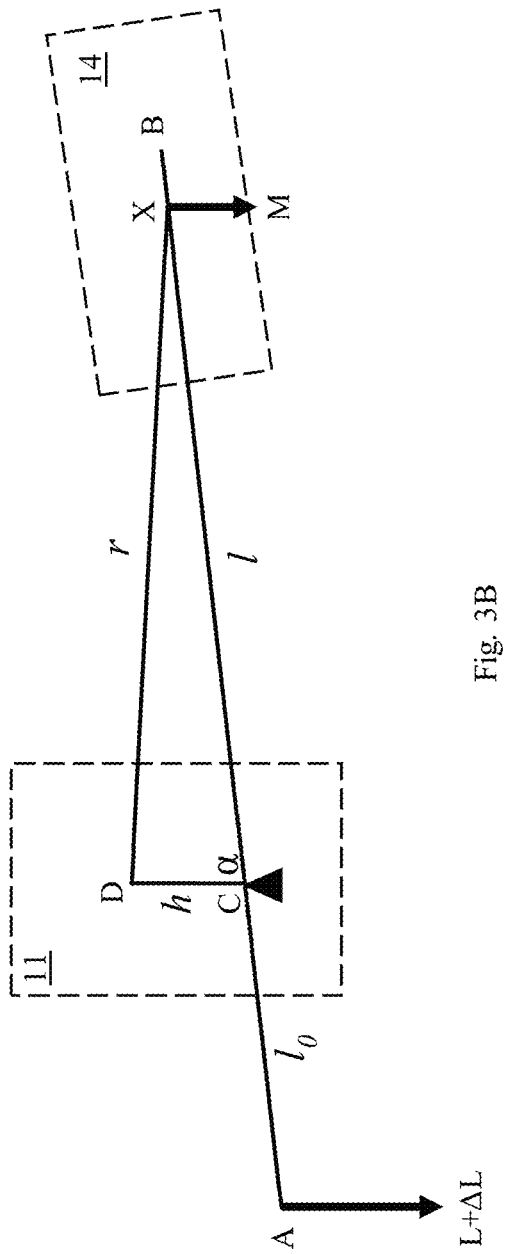
Figure 3C:
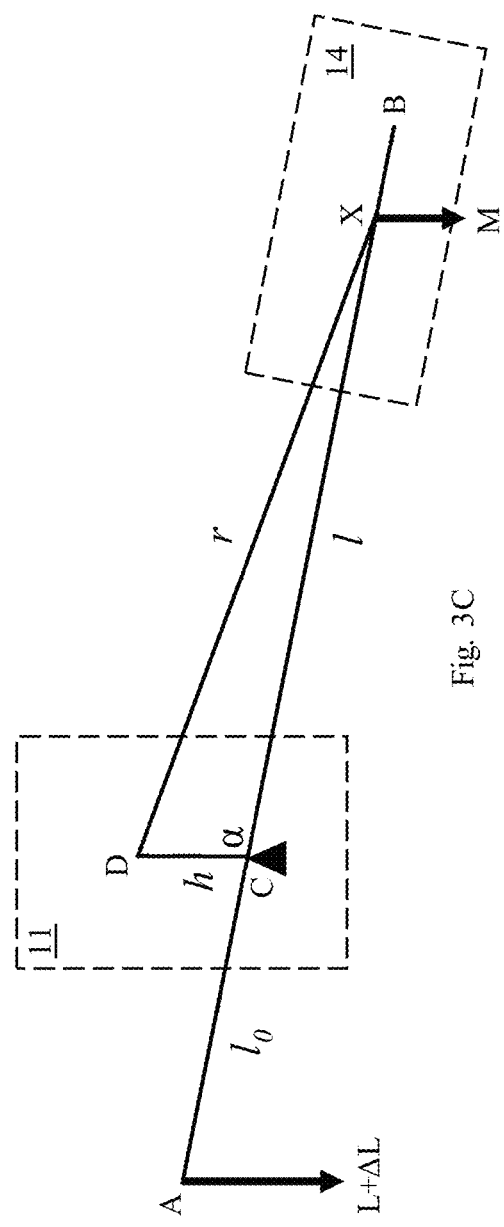

The precise relationship between the pivot angle of the balance beam 12 and the change of load required to balance the counterweight M is determined by the geometry of the counterbalance mechanism. FIGS. 3A-3C schematically illustrate a counterbalance mechanism that has a simpler geometry, showing how the lever arm length of the counterweight changes with the pivot angle of the balance beam. In this simpler geometry, point E, point F and point X in FIG. 2 collapse to the same point X in FIGS. 3A-C. This may be achieved, for example, by lowering the center of gravity of the counterweight 14 to coincide with the balance beam 12, and connecting the second end 16A of the link 16 to a point that coincides with the center of gravity. This simpler geometry is used here as an example to illustrate the general working principle of the counterbalance mechanism.

As shown in FIG. 3A, the counterbalance mechanism is adjusted such that when the balance beam AB is horizontal (with the line CD being vertical, and the angle DCB=90°), the counterweight M and the load L balance each other. This is referred to as the zero point. At the zero point, the length $l_1$ of line CX, i.e. the lever arm length for the counterweight M, is:

$$l_1 = \sqrt{r_2 - h^2}$$

where r is the length of line DX (i.e. the length of the mechanical link) and h is the length of line CD. The load L required to balance the counterweight M at the zero point is:

$$L = M * l_1 / l_0$$

where $l_0$ is the length of line AC, i.e. the lever arm length for the load. Note here that the above equation does not include the load that may be required to balance the weight of the balance beam 12 itself. Since this load is a constant, it is omitted in the rest of the discussions.

FIG. 3B illustrates a state of the counterbalance mechanism of FIG. 3A where the balance beam AB is pivoted away from the zero point in the counter-clockwise direction (i.e. the counterweight 14 is lifted), so that the angle DCB≡α<90°. This causes the counterweight 14 to slide away from the pivot C and lengthen the lever arm CX. The length l of line CX may be calculated as follows. From the law of cosines, $$r^2 = h^2 + l^2 - 2*h*l*\cos \alpha$$

i.e., $$l^2 - 2*h*l*\cos \alpha - r^2 + h^2 = 0$$

Applying the quadratic formula, the lever arm l is:

$$l = h*\cos\alpha + \sqrt{h^2 * \cos^2\alpha + r^2 - h^2} = h*\cos\alpha + \sqrt{h^2 * \cos^2\alpha + l_1^2}$$

The difference in lever arm length between the pivoted state of FIG. 3B and the zero point of FIG. 3A is:

$$\Delta l = l - l_1 = h*\cos \alpha + \sqrt{h^2*\cos^2\alpha + l_1^2} - l_1$$

When $h*\cos \alpha \ll l_1$, the above equation becomes:

$$\Delta l = h*\cos \alpha$$

In this pivoted state, an additional load ΔF is required at point A to balance the counterweight M:

$$(L+\Delta F)*l_0 = M*l$$

which gives:

$$\Delta F = M*\Delta l / l_0$$

At the pivoted state shown in FIG. 3B, because α<90°, Δl and ΔF are positive (i.e. ΔF is a downward force). FIG. 3C illustrates a state of the counterbalance mechanism where the balance beam 12 is pivoted away from the zero point in the clockwise direction (i.e. the counterweight 14 is lowered), so that the angle α>90°. The above-described equations hold for this state as well, but because α>90°, Δl and ΔF are now negative. In other words, from the zero point, a given amount of additional downward force at point A will push point A down to a new balance position, and a given amount of additional upward force at point A will push point A up to a new balance position.

It should be noted that the zero point of the counterbalancing mechanism is not limited to a horizontal balance beam 12 orientation. The counterbalancing mechanism can be design to have its zero point at any given pivot angle. What is important is the fact that the required load changes with the pivot angle of the balance beam 12.

For a more complex geometry, such as that shown in FIG. 2, the geometric analysis will be modified accordingly to calculate the required load as a function of the pivot angle α. Such analysis and calculation may be performed by those of ordinary skill in the mechanical art, based on the descriptions in this disclosure, without undue experimentation. A counterbalance mechanism can have any geometry, so long as the above-described geometric constraints are met.

For an ophthalmic laser system, the counterbalance mechanism is designed so that the patient interface device of the laser head exerts a downward force on the eye (referred to as the applanation force) during surgery. Thus, the load acting at the first end of the balance beam 12 is the sum of the weight (downward) of the laser head and a force (upward) exerted by the eye on the laser head (i.e. the counterforce of the applanation force). Because different patients and different ophthalmic procedures may require different amounts of applanation force, the goal of the counterbalance mechanism is to provide a desirable amount of applanation force that can be precisely controlled by varying the pivot angle of the balance beam.

The counterbalance mechanism may be designed so that when the balance beam 12 is at a predefined pivot angle (e.g., horizontal), the applanation force is a predefined amount. When the balance beam 12 pivots away from the predefined angle, the additional load 4F required to balance the counterweight 14 results in a change in the applanation force exerted on the eye, because the weight of the laser head is constant. In the geometry shown in FIGS. 2 and 3A-3C, for example, pivoting of the balance beam 12 in the counterclockwise direction results in a positive (i.e. downward) additional load being required to maintain balance, which results in a decrease in the applanation force on the eye. Conversely, pivoting of the balance beam 12 in the clockwise direction results in a negative (i.e. upward) additional load being required, which results in an increase in the applanation force on the eye. Thus, the counterbalance mechanism allows the amount of applanation force on the eye to be adjusted by changing the pivot angle of the balance beam 12.

The pivot angle α is related to the vertical distance s from point A to point C by:

$$\cos \alpha = s/l_0.$$

Here, the vertical distance s is defined as positive when point A is below point C. The vertical distance s may be referred to as the vertical travel of the laser head. Thus, the property of the counterbalance mechanism may also be expressed as a relationship between the applanation force and the vertical travel of the laser head. When $h^* \cos \alpha \ll l_1$, the equation of ΔF becomes:

$$\Delta F = M^* h^* s/l_0^2$$

In other words, when α is near 90°, the applanation force varies linearly with the vertical travel s and the slope of the linear relationship is determined by the geometry of the counterbalance mechanism.

Figure 4:
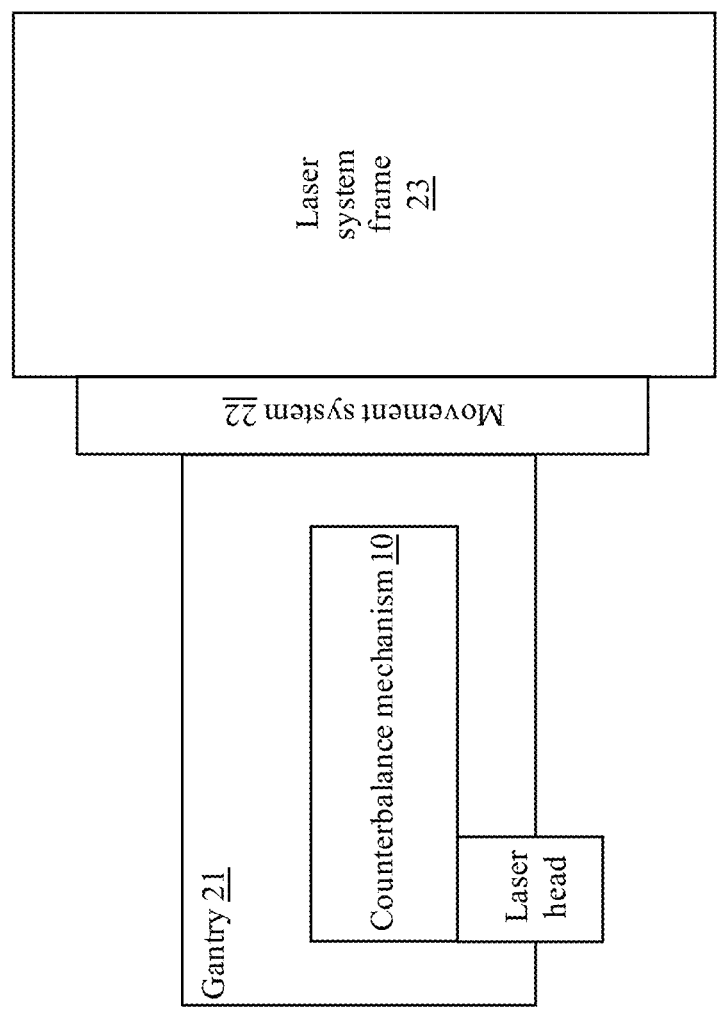
FIG. 4 schematically illustrates a portion of an ophthalmic laser system that incorporates the counterbalance mechanism according to embodiments of the present invention.

It should be noted that a change in the vertical travel of the laser head does not have to result in a change in the distance between the patient's eye and the laser head. This is because the support block 11 may itself be mounted on another movement system to allow it to move vertically. For example, the counterbalance mechanism may be located within a gantry of the laser system, with the support block fixedly attached to the gantry and the laser head partly protruding from the gantry. The gantry is supported by a movement system to allow it to move relative to the laser system's outer frame in at least the vertical direction, and preferably also in the horizontal directions. This movement system can facilitate docking of the laser head to the patient's eye in preparation for surgery. The movement system may be implemented by any suitable mechanical structure, such as rails, pivotable arms, telescoping arms, etc. In addition, the patient support bed that the patient is situated on may also be adjustable in height, which can change the distance between the eye and the laser head. Thus, for any given vertical travel of the laser head relative to the support block, the laser head and the patient's eye can be made to remain at a proper distance from each other for the patient interface device to engage the eye. FIG. 4 is a schematic block diagram that illustrate the relationship of the counterbalance mechanism 10, the laser head 17, the gantry 21, the movement system 22 and the frame 23 of the laser system.

In summary, a counterbalance mechanism according to embodiments of the present invention can have any geometry so long as the earlier-described geometric constraints are met. This allows for great freedom in designing the counterbalance mechanism to meet various requirements that may be imposed by practical considerations such as the size of the laser head.

In one particular example, the counterweight is M=5 kg, the lever arm of the load is $l_0$=100 mm, the lever arm of the counterweight at zero point is $l_1$=200 mm, the height of the connecting point of the link from the fulcrum h is about 39.5 mm (more generally, in the range of 35-45 mm), and the length of the link r is about 203.9 mm (more generally, in the range of about 203-205 mm). The applanation force is set at about 100 g at zero vertical travel of the laser head, and the change in applanation force ΔF is about 28-30 g per 1 mm change in vertical travel.

Various modifications may be made to the counterbalance mechanism described above. For example, although the balance beam 12 shown in FIGS. 2 and 3A-3C is straight, it may alternatively have a bent (angled) or curved shape. In another example, the center of gravity of the counterweight 14 may be located below the balance beam 12. The connection point 16B of the link 16 on the counterweight 14 may also be located below the balance beam 12.

In other alternative embodiments, the counterweight may be moved with an actuator, where the movement is controlled based on the desired amount of load, the desired position of the laser head, the desired applanation diameter, etc.

The counterbalance mechanism described above is applicable to any system that requires precise load variation as a function of distance of travel over a defined range.

Figure 5:
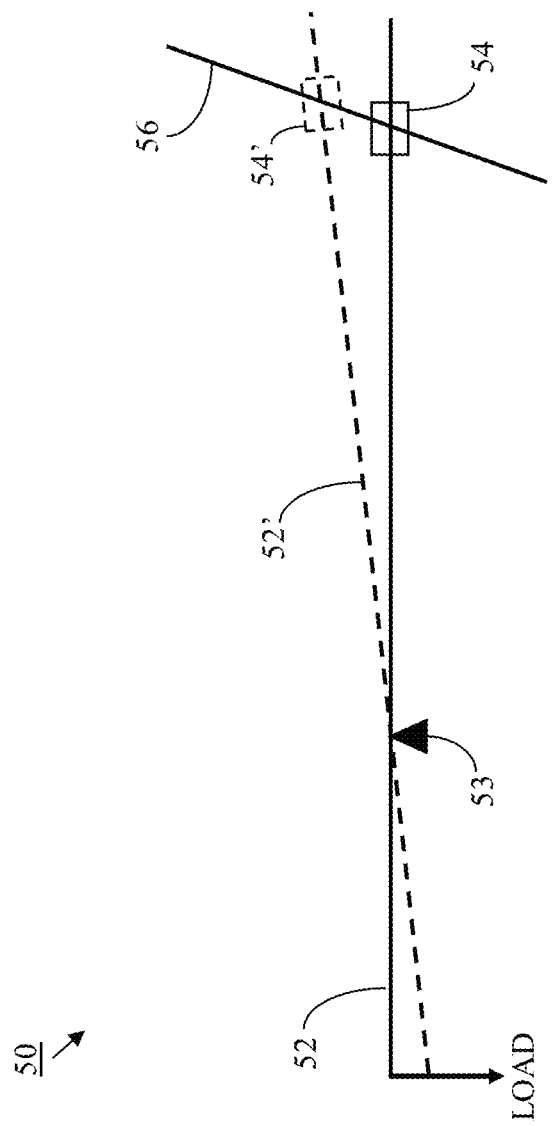
FIG. 5 schematically illustrates the geometric configuration (side view) of a counterbalance mechanism in an ophthalmic laser system according to an alternative embodiment of the present invention.

FIG. 5 schematically illustrates the geometric configuration (side view) of a counterbalance mechanism for a laser head in an ophthalmic laser system according to an alternative embodiment of the present invention. The counterbalance mechanism 50 includes a balance beam 52 supported by a fulcrum (pivot) 53. The laser head (LOAD) is attached to the balance beam 52 near the first end. A counterweight 54 is mounted on the balance beam near the second end via a linear motion bearing so that it is able to slide along the balance beam. The linear motion bearing is not shown in FIG. 5, but it may have a structure similar to the linear motion bearing 15 in FIG. 1. An inclined slot 56 is provided adjacent to the second end of the balance beam 52, and is inclined outwardly as it extends upwardly. A part of the counterweight 54, such as a protrusion or a pin, is disposed in the inclined slot 56 and is slidable along the slot.

When the balance beam 52 pivots around the pivot 53, due to the guidance by the inclined slot 56, the counterweight 54 moves along the balance beam 52. For example, when the balance beam pivots in a counter-clockwise direction as indicated by the dashed line labeled 52', the counterweight moves along the balance beam outwardly away from the pivot, as indicated by the dashed line object 54'. Conversely (not shown in the drawing), when the balance beam pivots in a clockwise direction, the counterweight moves along the balance beam inwardly toward the pivot.

This counterbalance mechanism produces a similar result as the counterbalance mechanism 10 of FIGS. 1-3, i.e., a counter-clockwise pivot of the balance beam 52 (i.e. a downward travel of the laser head relative to the fulcrum) results in a decrease in the applanation force on the eye, and a clockwise pivot of the balance beam 52 (i.e. an upward travel of the laser head relative to the fulcrum) results in an increase in the applanation force on the eye. The location and slope of the inclined slot 56 determine the zero point of the counterbalance mechanism and the slope of the applanation force as a function of the travel of the laser head. The location and slope of the inclined slot 56 may be made adjustable in order to adjust the zero point and other properties of the counterbalance mechanism. Similar to the embodiments of FIGS. 1-3C, the counterbalance mechanism may be designed so that when the balance beam 52 is at a predefined pivot angle (e.g., horizontal), the applanation force is a predefined amount.

Although the inclined slot 56 is shown in FIG. 5 as being a straight slot, in alternative embodiments, a curved (including multi-curved) inclined slot may be used, which achieve a non-linear function between the applanation force and the travel of the laser head.

It should be noted that FIG. 5 only illustrates the geometric configuration of the counterbalance mechanism 50. Those of ordinary skill in the art can implement this counterbalance mechanism by suitably modifying the structure shown in FIG. 1.

Figure 6:
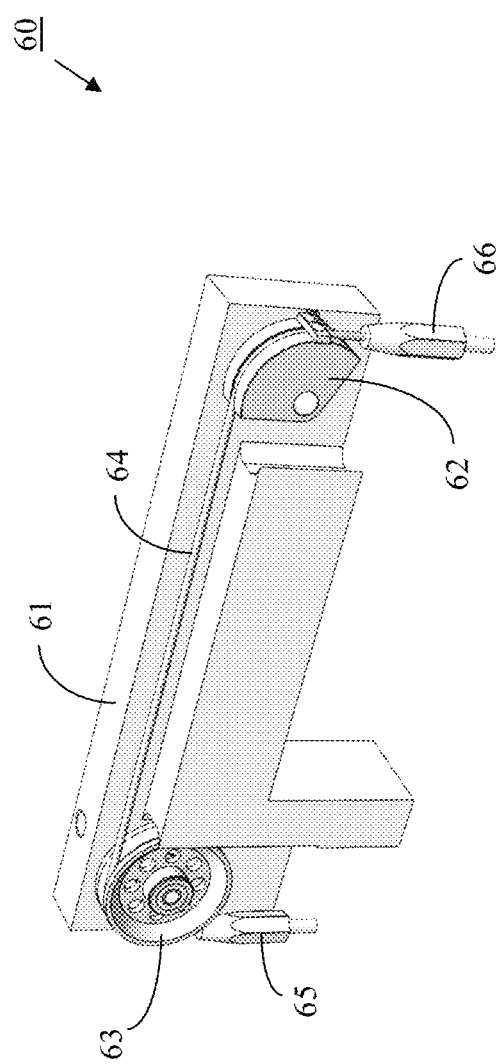
FIG. 6 schematically illustrates a counterbalance mechanism in an ophthalmic laser system according to another alternative embodiment of the present invention.

FIG. 6 schematically illustrates another alternative counterbalance mechanism for a laser head in an ophthalmic laser system. The counterbalance mechanism 60 employs an eccentric pulley 62 to achieve variable load counterweight mechanism. The eccentric pulley 62 is a pulley where the distance between the edge and the rotation axis is not a constant. A wire 64 runs over the eccentric pulley 62 and a circular pulley 63, both of which are mounted on a support block 61. The laser head 65 is attached to the end of the wire closer to the circular pulley 63, and the counterweight 66 is attached to the end of the wire closer to the eccentric pulley 62.

In this embodiment, the eccentricity of the pulley 62 determines the change in the load as a function of the distance traveled by the laser head. Preferably, the eccentric pulley 62 is designed such that a downward travel of the laser head 65 relative to the support block 61 results in a decrease in the applanation force on the eye, and an upward travel of the laser head results in an increase in the applanation force on the eye.

The counterbalance mechanisms in FIGS. 5 and 6 may be located in a gantry of the ophthalmic laser system, similar to the counterbalance mechanism 10 of FIG. 1.

It will be apparent to those skilled in the art that various modification and variations can be made in the counterbalance mechanism of the present invention without departing from the spirit or scope of the invention. Thus, it is intended that the present invention cover modifications and variations that come within the scope of the appended claims and their equivalents.

What is claimed is:

1. A ophthalmic laser system employing a counterbalance mechanism, comprising:
    a laser system frame;
    a gantry supported by the laser system frame; and
    a counterbalance system disposed within the gantry, including:
        a support block fixedly attached to the gantry;
        a balance beam pivotably mounted on the support block by a fulcrum, the balance beam having a first end and a second end located on opposite sides of the fulcrum;
        a laser beam delivery head attached to the balance beam near the first end;
        a counterweight;
        a bearing configured to mount the counterweight to the balance beam near the second end, wherein the counterweight is movable along the balance beam via the bearing; and
        an inclined slot disposed adjacent to the second end of the balance beam, the inclined slot being non-parallel to the balance beam and extending outwardly as it extends upwardly, wherein a part of the counterweight is disposed in the inclined slot and slidable along the inclined slot, wherein the inclined slot is configured to move the counterweight along the balance beam when the balance beam pivots around the fulcrum.

2. The ophthalmic laser system of claim 1, wherein the inclined slot is configured to move the counterweight along the balance beam away from the fulcrum when the balance beam pivots in a direction that lifts the counterweight, and to move the counterweight along the balance beam toward the fulcrum when the balance beam pivots in a direction that lowers the counterweight.

3. The ophthalmic laser system of claim 1, wherein the inclined slot is a straight slot and a position and a slope of the inclined slot are adjustable.

4. The ophthalmic laser system of claim 1, wherein the inclined slot is a curved slot.

5. The ophthalmic laser system of claim 1, wherein a weight of the laser beam delivery head and a weight of the counterweight are balanced when the balance beam is at a predefined pivot angle.

6. The ophthalmic laser system of claim 1, further comprising:
    a movement system configured to moveably support the gantry on the laser system frame, wherein the gantry is movable in at least a vertical direction relative to the laser system frame.

* * * * *